United States Patent [19]

Dorfman

[11] Patent Number: 5,365,874
[45] Date of Patent: Nov. 22, 1994

[54] END OF DENTAL FLOSS TAPE INDICATOR

[76] Inventor: Jason R. Dorfman, 1337 Oakmeadow Ct., Wheeling, Ill. 60090

[21] Appl. No.: 993,083

[22] Filed: Dec. 18, 1992

[51] Int. Cl.⁵ .......................... A61C 15/04; G08B 5/00
[52] U.S. Cl. .................................. 116/200; 116/205; 132/321
[58] Field of Search .............. 116/67 A, 200, 205, 116/278, DIG. 17; 242/1; 132/321, 324, 325

[56] References Cited

U.S. PATENT DOCUMENTS

| | | | |
|---|---|---|---|
| 1,935,970 | 11/1933 | Wooster et al. | 116/200 |
| 2,077,242 | 4/1937 | La Pierre | 116/200 |
| 2,809,458 | 10/1957 | Wilbourn | 43/1 |
| 3,158,938 | 12/1964 | Phillipps et al. | 33/733 |
| 3,592,203 | 7/1971 | Johnson | 132/323 |
| 3,897,796 | 8/1975 | Erickson | 132/321 |
| 3,930,059 | 12/1975 | Wells | 132/325 X |
| 4,646,766 | 3/1987 | Stallard | 132/325 |
| 4,901,663 | 2/1990 | De Luca | 116/200 |
| 5,159,943 | 11/1992 | Richards et al. | 132/321 |

Primary Examiner—William A. Cuchlinski, Jr.
Assistant Examiner—W. Morris Worth
Attorney, Agent, or Firm—Welsh & Katz, Ltd.

[57] ABSTRACT

An indicator of the end of a length of a tape of dental floss contained within a dispenser, the indicator being a segment of the length of tape having a different indicia or appearance than a prior segment of the length of tape. The indicator is located at a predetermined distance from an end of the tape to indicate that the length of the tape remaining within the dispenser is being depleted.

7 Claims, 1 Drawing Sheet

END OF DENTAL FLOSS TAPE INDICATOR

BACKGROUND OF THE INVENTION

This invention relates to dental floss in general and more particularly to an indicator of the approaching end of a tape or ribbon of dental floss.

Dental floss tape is widely used for the removal of germs and plaque from the surface of teeth, particularly on the surface area bordering the space between adjoining teeth.

Dental floss tape is typically sold in a certain length which is wound into a roll about a reel that is generally enclosed in a dispenser. The reel is mounted within the dispenser for rotational movement, thereby allowing the unwinding of a desired amount of floss from the reel. The enclosure also typically includes an element which will cut the tape after the desired length of tape has been unwound.

A drawback of these devices is that because of the enclosure, the user has difficulty in determining whether the supply of tape remaining in the roll is about to be depleted and a new supply of dental floss tape needs to be purchased.

To overcome this drawback, the enclosure may contain a peephole which allows visual ascertainment of the circumferential thickness of the roll thereby giving an approximate indication of the remaining length of dental floss on the reel. However, this arrangement presupposes the user will continually monitor the circumferential thickness during use of the reel. Such monitoring may not occur frequently enough to prevent the inadvertent depletion of the tape. Another drawback to visual monitoring occurs if the user is sightless or cannot otherwise make the ascertainment as to the length of floss remaining.

It is therefore an object of the present invention to provide an indication that the remaining length of dental tape within a dental floss dispenser is of such a length which necessitates the purchase of a new dispenser.

A related object is to provide an embodiment of such an indicator which can indicate to a sightless user that the remaining length of dental floss on the reel is of such a length which necessitates the purchase of a new dispenser.

SUMMARY OF THE INVENTION

Accordingly, an indicator of the end of a length of a tape of dental floss contained within a dispenser is provided with the indicator being a segment of the length of tape having a different indicia than a prior segment of the length of tape. The indicator is located at a predetermine distance from an end of the tape to indicate that the length of the tape within the dispenser is being depleted.

DESCRIPTION OF THE PREFERRED EMBODIMENTS

Figure 1:
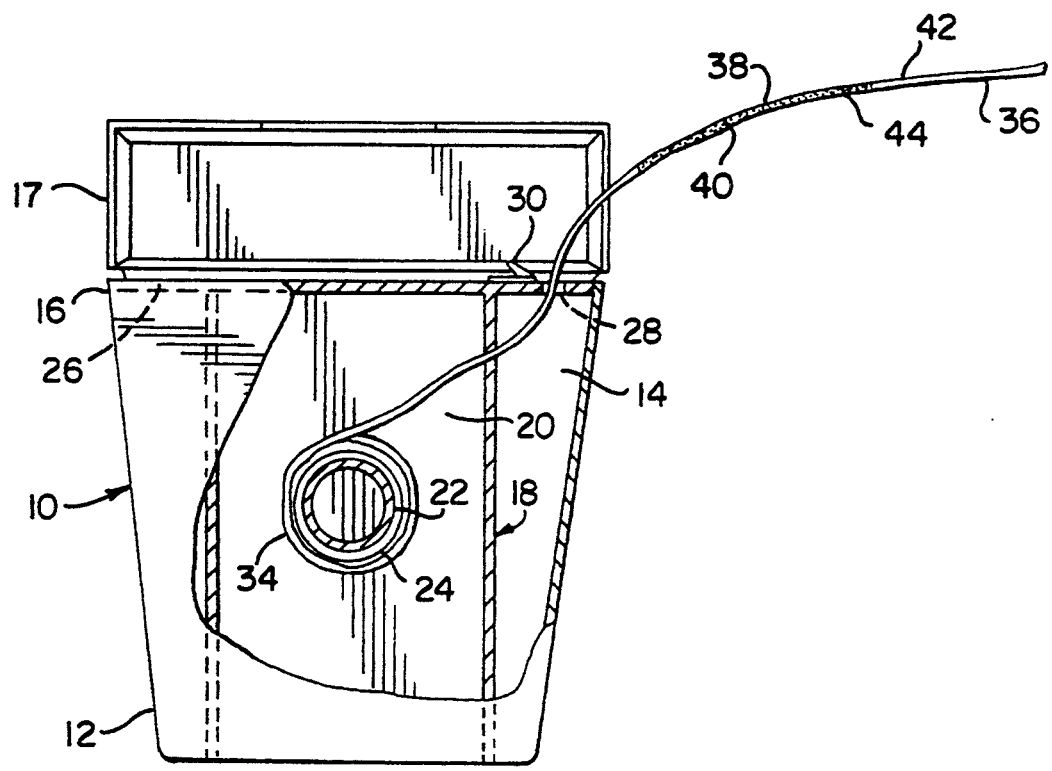
FIG. 1 is a front elevational view with parts removed of a dental floss tape dispenser having dental floss tape including the indicator of the present invention.

Referring to FIG. 1, a typical dental floss dispenser is indicated generally at 10. The dispenser 10 includes an elongated box-like housing 12 forming a containing cavity 14. Integrally attached to an upper edge 16 of the housing 12 is a cap 17 having a bottom end configured to snap about the upper edge 16 of the housing to hold the cap in a closed position.

Disposed within the cavity 14 is an insert 18 including a support wall 20 having a forward projecting cylinder shaped axle 22. Disposed for rotational movement about the axle 22 is a reel 24. The insert 18 also includes an upper horizontal flange 26 integrally attached to the upper edge of the support wall 20 and adapted to snugly fit within the upper edge 16 of the housing 12 and enclose the cavity 14. The flange 26 defines an orifice 28. Disposed on the upper surface of the flange 26 is a well known clipping device 30 for cutting dental floss tape or ribbon.

Wound about the reel 24 is a roll 34 comprised of a ribbon or tape 36 of dental floss. Lengths of the tape 36 extend and are pulled through the orifice 28 for use. The tape 36 includes a preferred embodiment of the end of tape indicator 38 of the present invention. The indicator 38 comprises at least one segment 40 of the tape 36 having an indicia or appearance which is different than a prior segment 42 of the tape which has been previously unwound from the roll 34. The segment 40 has a leading edge 44. In the preferred embodiment, the segment 40 is of a different color, shown by shading, than the prior segment 42. If desired, the segment 40 could be of a different material having a different texture than prior segment 42. The indicator 38 is placed at a predetermined location from the end of the tape 36 so as to indicate to the user that the tape remaining on the roll 34 is about to be depleted and a new supply of dental floss should be obtained. By way of example, the indicator 38 may show that the user has only a two day supply of floss remaining.

It is apparent that the indicator 38 may include a segment 40 which extends from the leading edge 44 to the end of the tape 36 whereby the leading edge of the segment is located at a predetermined location from the end of the tape. The leading edge 44 thereby indicates to the user that the tape remaining on the roll 34 is about to be depleted.

The length of the segment 40 of the indicator 38 is preferably 1 inch to provide a noticeable indicia while minimizing the manufacturing expense of creating the indicia. The coloring of the predetermined length may be accomplished by a dye which is non-toxic and will remain on the floss in the presence of saliva.

Figure 2:
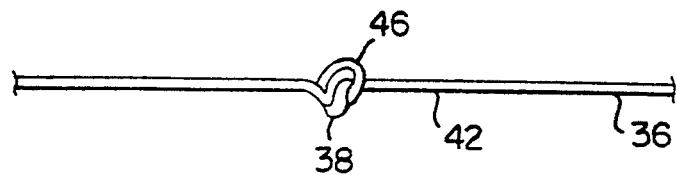
FIG. 2 is a front elevational of a section of a dental floss including an alternate embodiment of the indicator of the present invention.

Referring to FIG. 2, an alternate embodiment of the segment 40 is shown with the indicia formed by the segment 40 having a different physical structure, such as a knot 46, than the prior segment 42 of the length of dental floss. The knot 46 is located along the length of dental floss tape 36 at a predetermined distance from the end of the roll 34 of tape. The predetermined distance is selected to indicate to the user that the length of dental floss 36 remaining on the roll 34 is about to be depleted and a new supply of dental floss should be obtained.

To insure the knot 46 draws the attention of the user, the knot may be made of a dimension which will cause a momentary snagging of the knot on the upper flange 26 of the insert as the tape 36 is pulled through the orifice 28. However, the knot 46 should be constructed so that the user may supply sufficient tension to force the knot to travel through the orifice 28 after snagging.

In operation, the user employs the tape 36 of dental floss by sequentially pulling lengths of tape from the reel through the orifice 28 and cutting the tape on the clipping device 30. Eventually the roll 36 of tape will be depleted to a point such that upon the user pulling out a desired length of tape, the indicator 38 will be exposed and indicate to the user that a new supply of dental floss tape should be purchased.

For normal usage, the color differential embodiment of FIG. 1 is suitable for providing an indication that exhaustion of the supply of dental tape 36 is imminent. The embodiment of the invention illustrated in FIG. 2 is particularly adapted to allow sightless or minimal sighted persons to use the sense of feel to be advised when the reel of tape 36 is almost empty.

Specific embodiments of the novel dental floss end of tape indicator according to the present invention has been described for the purposes of illustrating the manner in which the invention may be made and used. It should be understood that implementation of other variations and modifications of the invention in its various aspects will be apparent to those skilled in the art and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. An indicator of depletion of a length of a tape of dental floss contained within an adapted to be fed sequentially from a dispenser, said indicator comprising: an indicating segment of the length of tape having one of an indicia and an appearance different from a prior segment of the length of tape to be fed from said dispenser, said indicating segment being located at a predetermined distance from an end of the tape to indicate that the length of the tape remaining within the dispenser is nearing depletion.

2. The indicator of claim 1 wherein said indicating segment is a different color than said prior segment.

3. The indicator of claim 1 wherein said indicating segment has a different physical configuration than said prior segment.

4. The indicator of claim 3 wherein said indicating segment is a knot.

5. The indicator of claim 3 wherein said indicating segment is a different material than said prior segment.

6. The indicator of claim 3 wherein said indicating segment has a different texture than said prior segment.

7. An indicator of depletion of a length of a tape of dental floss contained within and adapted to be fed sequentially from a dispenser, said indicator comprising: an indicating segment of the length of tape having one of an indicia and an appearance different from a prior segment of the length of tape to be fed from said dispenser, said indicating segment having a leading edge located at a predetermined distance from an end of the tape to indicate that the length of the tape remaining within the dispenser is nearing depletion.

* * * * *